United States Patent
Skinner et al.

(10) Patent No.: US 9,797,825 B2
(45) Date of Patent: Oct. 24, 2017

(54) OPTICAL COMPUTING DEVICES WITH BIREFRINGENT OPTICAL ELEMENTS

(71) Applicant: Halliburton Energy Services, Inc., Houston, TX (US)

(72) Inventors: Neal Gregory Skinner, Lewisville, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 58 days.

(21) Appl. No.: 14/434,650

(22) PCT Filed: Jun. 12, 2013

(86) PCT No.: PCT/US2013/045384
§ 371 (c)(1),
(2) Date: Apr. 9, 2015

(87) PCT Pub. No.: WO2014/200474
PCT Pub. Date: Dec. 18, 2014

(65) Prior Publication Data
US 2015/0276582 A1    Oct. 1, 2015

(51) Int. Cl.
*G01J 4/00*     (2006.01)
*G01N 21/23*    (2006.01)
(Continued)

(52) U.S. Cl.
CPC ......... *G01N 21/23* (2013.01); *G01B 11/0625* (2013.01); *G01N 21/314* (2013.01); *G02B 5/3083* (2013.01); *G01N 2201/0683* (2013.01)

(58) Field of Classification Search
CPC ....................................................... G01J 4/00
(Continued)

(56) References Cited

U.S. PATENT DOCUMENTS 3,839,067 A * 10/1974 Sosnowski .............. G02F 1/065
                                                             385/130
4,520,189 A    5/1985 Rogers et al.
(Continued)

FOREIGN PATENT DOCUMENTS

EP          0488544 A1    6/1992
JP       2004-301891 A   10/2004
(Continued)

OTHER PUBLICATIONS

Supplementary Partial European Search Report completed Oct. 28, 2016 in EP13886749.
(Continued)

*Primary Examiner* — Roy M Punnoose
(74) *Attorney, Agent, or Firm* — McDermott Will & Emery LLP

(57) ABSTRACT

Disclosed are optical computing devices that employ birefringent optical elements configured for use in optical computing devices. One optical computing device includes a polarizer configured to generate at least x polarized light and y polarized light, a birefringent integrated computational element configured to optically interact with a substance and the polarizer, thereby generating optically interacted light, and at least one detector arranged to receive the optically interacted light and generate an output signal corresponding to a characteristic of the substance.

33 Claims, 4 Drawing Sheets

(51) Int. Cl.
  *G01N 21/31* (2006.01)
  *G01B 11/06* (2006.01)
  *G02B 5/30* (2006.01)

(58) Field of Classification Search
  USPC .......................................................... 356/365
  See application file for complete search history.

(56) References Cited

U.S. PATENT DOCUMENTS

| | | | |
|---|---|---|---|
| 4,707,147 A | 11/1987 | Aoki et al. | |
| 6,486,997 B1* | 11/2002 | Bruzzone | B29C 55/023 349/9 |
| 6,529,276 B1 | 3/2003 | Myrick | |
| 6,926,410 B2* | 8/2005 | Weber | G02B 27/283 353/20 |
| 7,138,156 B1* | 11/2006 | Myrick | G02B 5/285 359/359 |
| 8,345,234 B2* | 1/2013 | Myrick | G01J 3/02 356/300 |
| 8,912,477 B2 | 12/2014 | Freese et al. | |
| 9,041,932 B2* | 5/2015 | Priore | G01N 21/255 356/301 |
| 2004/0246874 A1* | 12/2004 | Takagi | G02B 27/0944 369/112.15 |
| 2005/0001983 A1* | 1/2005 | Weber | G02B 27/283 353/20 |
| 2007/0247635 A1 | 10/2007 | Kruger et al. | |
| 2007/0273880 A1 | 11/2007 | Sakai et al. | |
| 2010/0090112 A1 | 4/2010 | Kawada et al. | |
| 2013/0284895 A1 | 10/2013 | Freese et al. | |
| 2013/0284897 A1 | 10/2013 | Freese et al. | |
| 2013/0284898 A1* | 10/2013 | Freese | G01N 21/17 250/208.2 |
| 2013/0321813 A1* | 12/2013 | Treado | G01J 3/51 356/416 |

FOREIGN PATENT DOCUMENTS

| | | |
|---|---|---|
| KR | 10-2008-0031589 | 4/2008 |
| KR | 20130019071 A | 2/2013 |
| WO | 2005036215 A2 | 4/2005 |
| WO | 2007076338 A2 | 7/2007 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |

OTHER PUBLICATIONS

Nelson et al., Multivariate Optical Computation for Predictive Spectroscopy, Anal. Chem. 1998, 70, 73-82.
International Search Report and Written Opinion for PCT/US2013/045384 dated Mar. 12, 2015.

* cited by examiner

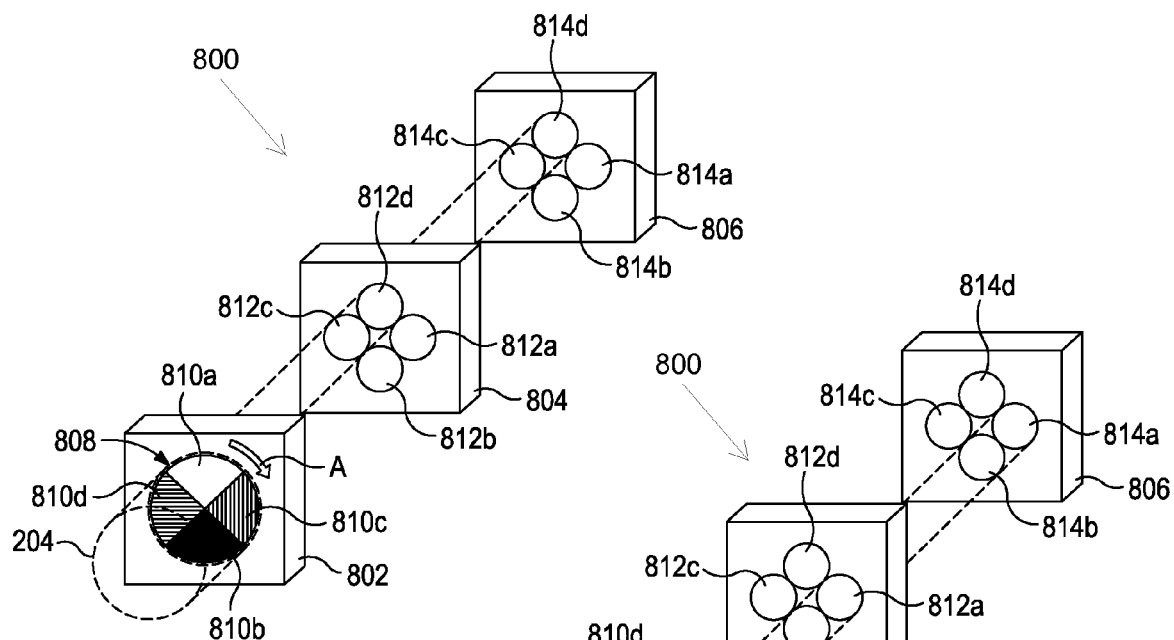
FIG. 8a
FIG. 8b
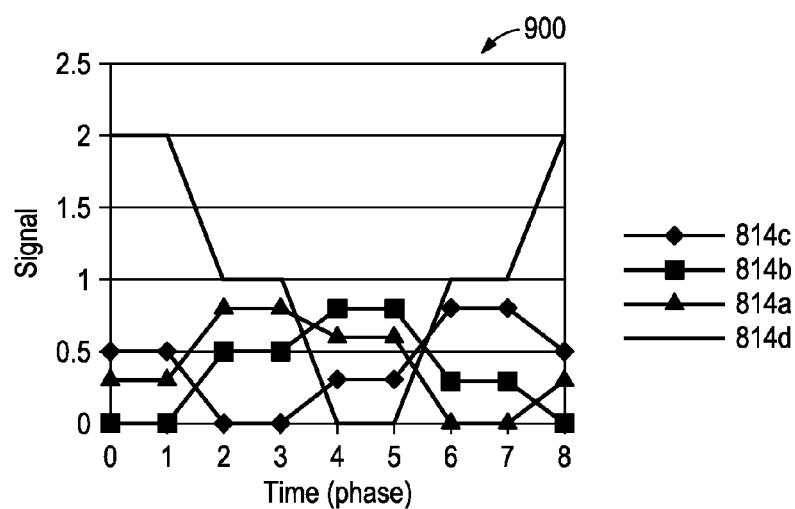
FIG. 9

OPTICAL COMPUTING DEVICES WITH BIREFRINGENT OPTICAL ELEMENTS

This application is a National Stage entry of and claims priority to International Application No. PCT/US2013/045384, filed on Jun. 12, 2013.

BACKGROUND

The subject matter of this disclosure generally relates to optical computing devices and, more particularly, to birefringent optical elements configured for use in optical computing devices.

Optical computing devices, also commonly referred to as "opticoanalytical devices," can be used to analyze and monitor a substance in real time. Such optical computing devices will often employ an optical processing element that optically interacts with the substance or a sample thereof to determine quantitative and/or qualitative values of one or more physical or chemical properties of the substance. The optical element may be, for example, an integrated computational element (ICE), also known as a multivariate optical element (MOE), which includes an optical interference filter that can be designed to operate over a continuum of wavelengths in the electromagnetic spectrum from the ultraviolet (UV) to mid-infrared (MIR) ranges, or any sub-set of that region. Electromagnetic radiation that optically interacts with the ICE is changed so as to be readable by a detector, such that an output of the detector can be correlated to a physical or chemical property of the substance being analyzed.

An ICE (hereafter "ICE component") typically includes a plurality of optical layers that include various materials whose index of refraction and size (e.g., thickness) may vary between each layer. An ICE design refers to the number and thickness of the respective layers of the ICE component. The layers may be strategically deposited and sized so as to selectively pass predetermined fractions of electromagnetic radiation at different wavelengths, being configured to substantially mimic a regression vector corresponding to a particular physical or chemical property of interest of a substance. Accordingly, an ICE design will exhibit a transmission function that is weighted with respect to wavelength. As a result, the output light intensity from the ICE component conveyed to the detector may be related to the physical or chemical property of interest for the substance.

To date, the several layers that make up the ICE component are typically made from isotropic materials, or materials whose refractive indices are independent of the polarization state or the direction vectors of light propagating through them.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 8A and 8B illustrate an optical train that may be used in an optical computing device, according to one or more embodiments.

FIG. 9 depicts a line graph depicting resulting sensor signals derived from the optical train of FIGS. 8A and 8B.

DETAILED DESCRIPTION

Figure 1:
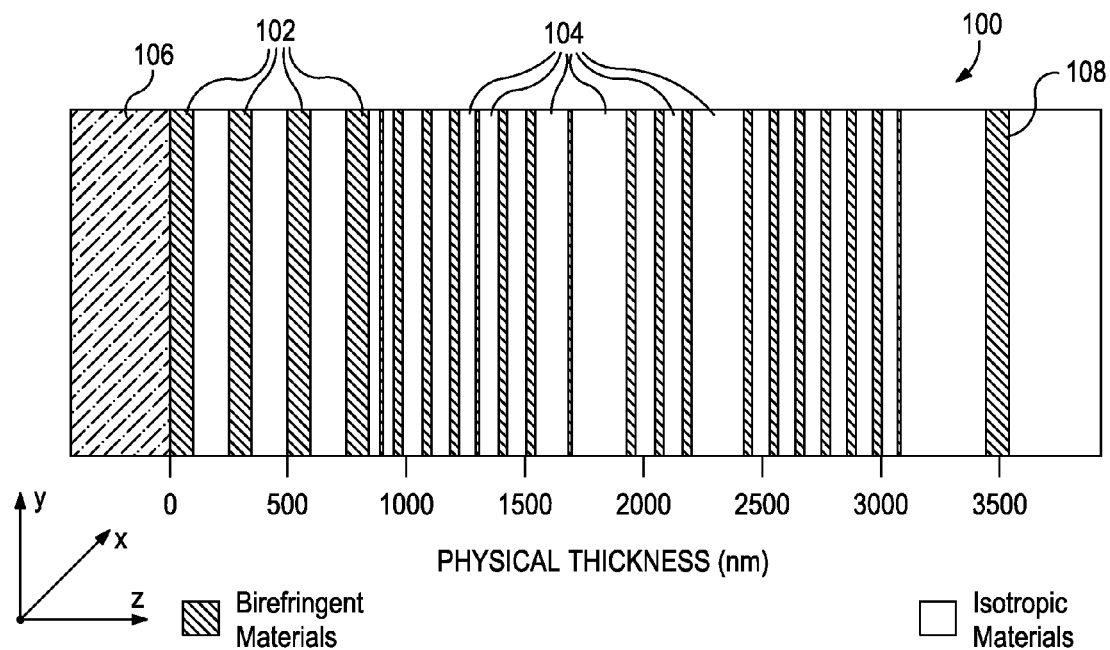
FIG. 1 illustrates an exemplary integrated computation element, according to one or more embodiments.

The subject matter of this disclosure generally relates to optical computing devices and, more particularly, to birefringent optical elements configured for use in optical computing devices.

The present disclosure expands the design options for optical elements, such as integrated computational elements (ICE). Whereas before ICE components have been designed and manufactured with several thin film layers made of optically isotropic materials, the embodiments disclosed herein describe ICE components that may incorporate one or more thin film layers made of birefringent materials. As known to those skilled in the art, birefringent materials are optically anisotropic materials whose refractive index depends on the state of polarization and the direction of propagation of electromagnetic radiation (e.g., light) transmitted through the material. The simplest birefringent materials are referred to as uniaxial materials and possess an optical axis such that rays propagating parallel to this axis are subject to the same refractive index, regardless of polarization. In general, rays propagating in directions not parallel to the optical axis will be subject to a refractive index that depends on both the direction of propagation and the polarization of the ray. If ray propagation is assumed along a z axis perpendicular to the optic axis, x polarized light is subject to one refractive index while y polarized light is subject to another. Biaxial materials also exist; however, the dependency of direction and polarization vectors on refractive index in these materials is much more complicated. Accordingly, the exemplary birefringent ICE components described herein are able to measure the concentrations of two different analytes or characteristics, one in response to x polarized light and the second in response to y polarized light.

An added benefit or advantage gained by using ICE components made with birefringent materials is that the changes in the refractive index can be used to correct for environmental effects, like temperature. As the temperature of an ICE component increases, for example, it experiences both a change in refractive index (dN/dT) and a change in thickness due to expansion. In some materials that make up traditional ICE components, these effects can be quite large and have a large impact on the resulting transmission profile of the ICE component, thereby leading to a detrimental prediction performance. According to embodiments disclosed herein, instead of employing complicated temperature correction protocols to overcome these temperature effects, optical computing devices incorporate birefringent ICE components, which can be used to alter the transmission profile of the ICE component to correct for dN/dT and expansion/contraction effects due to temperature fluctuations. As a result, each ICE component can be used over a broader temperature range.

The disclosed systems and methods may be suitable for designing and fabricating ICE components for use in the oil and gas industry. It will be appreciated, however, that the various disclosed systems and methods are equally applicable to designing and fabricating ICE components for use in other technology fields including, but not limited to, the food and drug industry, industrial applications, mining industries, or any field where it may be advantageous to determine in real-time or near real-time a characteristic of a specific substance, but where the environmental factors, such as temperature, pressure, and humidity, may have a critical impact in monitoring applications.

As used herein, the term "characteristic" refers to a chemical, mechanical, or physical property of a substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be monitored with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacterial content, total hardness, combinations thereof, state of matter (solid, liquid, gas, emulsion, mixtures, etc.), and the like.

As used herein, the term "substance," or variations thereof, refers to at least a portion of matter or material of interest to be tested or otherwise evaluated using the optical computing devices described herein. The substance includes the characteristic of interest, as defined above. The substance may be any substance capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, a treatment fluid, a fracturing fluid, a formation fluid, or any oilfield fluid, chemical, or substance as found in the oil and gas industry. The substance may also refer to a solid material such as, but not limited to, rock formations, concrete, solid wellbore surfaces, and solid surfaces of any wellbore tool or projectile (e.g., balls, darts, plugs, etc.).

As used herein, the term "electromagnetic radiation" refers to radio waves, microwave radiation, terahertz, infra-red and near-infrared radiation, visible light, ultraviolet light, X-ray radiation and gamma ray radiation.

As used herein, the term "optical computing device" refers to an optical device that is configured to receive an input of electromagnetic radiation associated with a substance and produce an output of electromagnetic radiation from a processing element arranged within the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the substance, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components), a substance being analyzed by the processing elements, or a polarizer used in an optical computing device. Accordingly, optically interacted light refers to electromagnetic radiation that has been reflected, transmitted, scattered, diffracted, or absorbed by, emitted, or re-radiated, for example, using a processing element, but may also apply to optical interaction with a substance or a polarizer.

As mentioned above, the processing element used in the above-defined optical computing devices may be an ICE component. In operation, an ICE component is capable of distinguishing electromagnetic radiation related to a characteristic of interest of a substance from electromagnetic radiation related to other components of the substance. Referring to FIG. 1, illustrated is an exemplary ICE 100, according to one or more embodiments of the present disclosure. As illustrated, the ICE 100 may include a plurality of alternating layers 102 and 104. The first plurality of layers 102 may be made of one or more anisotropic materials (i.e., birefringent materials) and the second plurality of layers 104 may be made of one or more isotropic materials.

Exemplary uniaxial birefringent materials that may be used as one or more of the first plurality of layers 102 include, but are not limited to, beryl ($Be_3Al_2(SiO_3)_6$), calcite ($CaCO_3$), calomel ($Hg_2Cl_2$), ice ($H_2O$), lithium niobate ($LiNbO_3$), magnesium fluoride ($MgF_2$), quartz ($SiO_2$), ruby ($Al_2O_3$), rutile ($TiO_2$), sapphire ($Al_2O_3$), sodium nitrate ($NaNO_3$), tourmaline, zircon (high and low $ZrSiO_4$), silicon carbide (Moissanite), plastics (e.g., cellophane, polystyrene, polycarbonate, and the like), combinations thereof, and the like. Exemplary biaxial birefringent materials that may be used as one or more of the first plurality of layers 102 include, but are not limited to, borax ($Na_2(B_4O_5)(OH)_48(H_2O)$), epsom salt ($MgSO_47(H_2O)$), biotite ($K(Mg,Fe)_3AlSi_3O_{10}(FOH)_2$), muscovite ($KAl_2(AlSi_3O_{10})(FOH)_2$), olivine (($(Mg,Fe)_2SiO_4$), perovskite ($CaTiO_3$), topaz ($Al_2SiO_4(FOH)_2$), ulexite ($NaCaB_5O_6(OH)_65(H_2O)$).

Exemplary isotropic materials that may be used as one or more of the second plurality of layers 104 include, but are not limited to, silicon, silica, quartz ($SiO_2$), niobia and niobium, germanium and germania, MgF, SiO, and other high and low index materials or glasses known in the art.

The layers 102, 104 may be strategically deposited on an optical substrate 106. In some embodiments, the optical substrate 106 is BK-7 or another optical glass. In other embodiments, the optical substrate 106 may be another type of optical substrate which may or may not be birefringent, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation, and may be able to detect a sample substance. Layer 108 may or may not be birefringent. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be noted that while the layers 102, 104 are shown as alternating between each other in single layer increments, it is also contemplated herein that two or more layers 102, 104 of either isotropic or anisotropic materials may be arranged together and otherwise alternating with the other materials. Moreover, in at least one embodiment, the isotropic layers 104 may be omitted from the ICE 100 altogether and the ICE 100 may instead include only a single or multiple anisotropic layers 102, without departing from the scope of the disclosure.

In some embodiments, one or more of the anisotropic layers 102 may be created or otherwise generated from an isotropic layer 104 or from an isotropic material as defined above. For instance, isotropic materials generally do not exhibit birefringence, but when placed under mechanical stress, some isotropic materials may become birefringent. This is often referred to as "stress induced birefringence" or simply "stress birefringence." In at least one embodiment, an isotropic material or layer 104 may be stressed, such as between upper and lower plates or a vice, such that an anisotropic stress is applied to the layer 104. As a result, the layer 104 may exhibit birefringence and otherwise act similar to a birefringent layer 102, as generally described above. Accordingly, it is contemplated herein that the ICE 100 be made of one or more stress induced birefringent materials, where an isotropic material is mechanically stressed to exhibit birefringence.

It should be understood that the exemplary ICE 100 in FIG. 1 does not in fact represent any particular ICE component configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the birefringent and/or isotropic materials of each layer 102, 104 can be doped or two or more birefringent or isotropic materials can be combined in a manner to achieve the desired optical characteristic. In at least one embodiment, as mentioned above, both layers 102, 104 may be made of birefringent materials, without departing from the scope of the disclosure. In addition to solid materials used for the layers 102, 104, the exemplary ICE 100 may also contain one or more birefringent and/or isotropic layers 102, 104 that are liquid and/or gases, optionally in combination with solid layers 102, 104. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 exhibit different refractive indices. By properly selecting the materials of each layer 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength may be set to the regression weightings described with respect to a known equation, data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE 100 may be configured to perform the dot product of the received electromagnetic radiation and the wavelength dependent transmission function of the ICE 100. The wavelength dependent transmission function of the ICE is dependent on the layer material refractive index, the number of layers 102, 104 and thickness of each layer 102, 104. The ICE 100 transmission function is then analogous to a desired regression vector derived from the solution to a linear multivariate problem targeting a specific component of the substance being analyzed. As a result, the output light intensity of the ICE 100 is related to the characteristic or analyte of interest of the substance.

Optical computing devices employing the ICE 100 may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time.

As depicted in FIG. 1, each individual layer 102, 104 is arranged perpendicular to the z-axis of the ICE 100. When properly designed, with a combination of birefringent layers 102 and isotropic layers 104, the ICE 100 may be configured to exhibit or otherwise generate two pairs of reflection and transmission spectra, one for x polarized light and one for y polarized light propagating along the z direction through the stack of layers 102, 104. Accordingly, the present disclosure provides a single ICE component (i.e., the ICE 100) that may be configured to measure or detect concentrations of at least two different characteristics or analytes, a first analyte in response to x polarized light and a second analyte in response to y polarized light.

Figure 2:
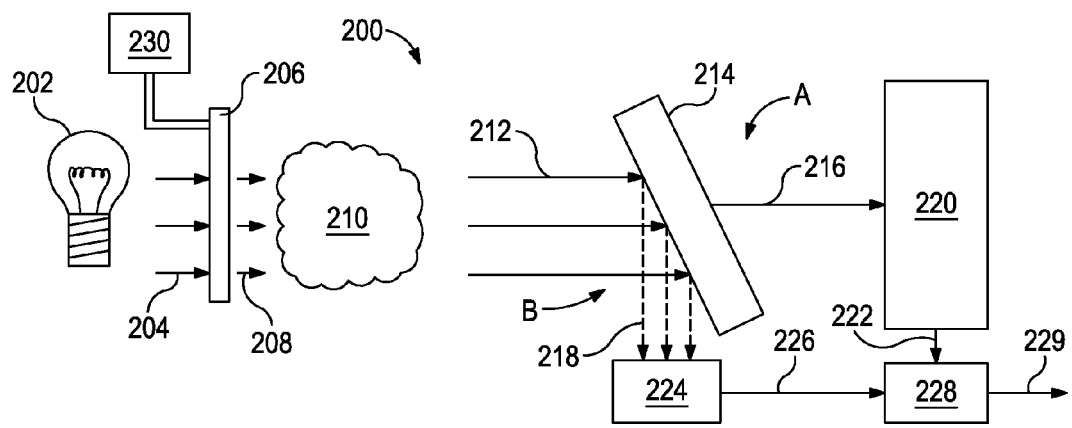
FIG. 2 illustrates an exemplary optical computing device, according to one or more embodiments.

Referring now to FIG. 2, with continued reference to FIG. 1, illustrated is an exemplary optical computing device 200, according to one or more embodiments of the present disclosure. As illustrated, the optical computing device 200

(hereafter "device 200") may include an electromagnetic radiation source 202 that emits or otherwise generates electromagnetic radiation 204. The electromagnetic radiation source 202 may be any device capable of emitting or generating the electromagnetic radiation 204 as defined herein. In some embodiments, for example, the electromagnetic radiation source 202 may be, but is not limited to, a light bulb, a light emitting diode (LED), a laser, a blackbody, a photonic crystal, a terahertz source, an X-Ray source, a laser pumped continuum source, combinations thereof, or the like. In at least one embodiment, the electromagnetic radiation 204 emitted from the source 202 may be unpolarized light.

In some embodiments, the electromagnetic radiation 204 may be directed toward and otherwise transmitted through a polarizer 206. The polarizer 206 may be, for example, a linear polarizer, but may also be any other type of optical filter configured to pass light of a specific polarization and simultaneously block waves of other polarizations. Polarized light 208 may be emitted from or otherwise pass through the polarizer 206.

In the illustrated embodiment, the polarized light 208 may be directed toward a substance 210, or a sample of the substance 210, which may contain a characteristic or analyte of interest. The polarized light 208 may optically interact with the substance 210 and produce or generate sample interacted light 212 or a beam of sample interacted light 212. It should be noted that while FIG. 2 shows the polarized light 208 as passing through the substance 210 to produce the sample interacted light 212, it is also contemplated herein to reflect the polarized light 208 off of the substance 210, such as may be required when the substance 210 is translucent, opaque, or solid. Accordingly, reflecting the polarized light 208 off of the substance 210 may equally generate the sample interacted light 212.

Although not specifically shown, one or more spectral elements may be employed in the device 200 in order to restrict the optical wavelengths and/or bandwidths of the system, and thereby eliminate unwanted electromagnetic radiation existing in wavelength regions that have no importance. Such spectral elements can be located anywhere along the optical train, but are typically employed directly after the electromagnetic radiation source 202.

The optical computing device 200 may further include an ICE 214 which, in the illustrated embodiment, may be configured to receive and optically interact with the sample interacted light 212. The ICE 214 may be substantially similar to the ICE 100 of FIG. 1, having both birefringent and isotropic layers, and may be referred to herein as "the birefringent ICE 214." In the illustrated embodiment, the ICE 214 may serve partially as a beam splitter configured to receive and split the sample interacted light 212 into transmitted light 216 directed in a first channel A and reflected light 218 directed in a second channel B. As used herein, the term "channel" refers generally to an optical path or optical train, as known in the art.

The transmitted light 216 may be characterized as modified electromagnetic radiation that corresponds to the characteristic of interest for the substance 210. In particular, the transmitted light 216 may include electromagnetic radiation or light that has optically interacted with the birefringent ICE 214, whereby an approximation of the regression vector corresponding to the characteristic of interest is obtained.

Within the first channel A, the transmitted light 216 may be conveyed to a first detector 220 for quantification of the resulting signal. The first detector 220 may be any device capable of detecting electromagnetic radiation, and may be generally characterized as an optical transducer. For example, the first detector 220 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, a terahertz detector, combinations thereof, or the like, or other detectors known to those skilled in the art.

In some embodiments, the first detector 220 may be configured to produce an output signal 222 in the form of a voltage (or current) that corresponds to the particular characteristic of the substance 210. In at least one embodiment, the output signal 222 produced by the first detector 220 and the concentration of the characteristic of the substance 210 may be directly proportional. In other embodiments, however, the relationship may correspond to a polynomial function, an exponential function, a logarithmic function, and/or any combination thereof.

The reflected light 218 may be directed within the second channel B toward a second detector 224. The second detector 224 may be similar to the first detector 220 and therefore capable of detecting electromagnetic radiation. In some embodiments, the second detector 224 may be used to detect radiating deviations stemming from the electromagnetic radiation source 202. Radiating deviations can include such things as intensity fluctuations in the electromagnetic radiation 204, interferent fluctuations (e.g., dust or other interferents passing in front of the electromagnetic radiation source 202), coatings on windows or lenses included with the optical computing device 200, combinations thereof, or the like. Without proper signal compensation, such radiating deviations could result in inaccurate measurements for the device 200 as derived through the primary channel A and its corresponding output signal 222.

To correct or compensate for radiating deviations, the second detector 224 may be configured to generate a compensating signal 226 generally indicative of the radiating deviations of the electromagnetic radiation source 202. Accordingly, the second channel B may be characterized as or otherwise referred to as a "reference" channel. In some applications, the compensating signal 226 and the output signal 222 may be transmitted to or otherwise received by a signal processor 228 communicably coupled to both the detectors 220, 224. The signal processor 228 may be a computer including a non-transitory machine-readable medium and may be configured to computationally combine the compensating signal 226 with the output signal 222 in order to normalize the output signal 222 in view of any radiating deviations detected by the second detector 224. In some embodiments, computationally combining the output and compensating signals 222, 226 may entail computing a ratio of the two signals 222, 226, thereby essentially computing a ratio of the primary and reference channels A and B (e.g., A/B).

It will be appreciated that in some embodiments the function of the first and second detectors 220 and 224 may be reversed, without departing from the scope of the disclosure. That is, the second detector may be used to generate the output signal 222, and the first detector 220 may be used as a reference detector to provide the compensating signal 226 that normalizes the output signal 222. Several variations of the device 200 that may be implemented while nonetheless remaining within the scope of the disclosure.

Using the signal processor 228, the characteristic(s) of the substance 210 being analyzed with the device 200 can be determined and further processed computationally to provide additional characterization information about the substance 210. In some embodiments, for example, the identification and concentration of each analyte in the substance 210 can be used to predict certain physical characteristics of the substance 210. The bulk characteristics of a substance 210 can be estimated by using a combination of the properties conferred to the substance 210 by each analyte. This data may be compiled and conveyed from the signal processor 228 to a user for consideration in the form of a resulting output signal 229. In some embodiments, the resulting output signal 229 may be conveyed to a computer system (not shown) having one or more peripheral devices, such as a monitor or a printer, configured to provide a graphical output depicting the characteristic(s) detected in the substance 210.

According to the present disclosure, the polarizer 206 may be rotatable such that varying directions of polarized light 208 may be emitted from the polarizer 206, depending on its particular angle of rotation. In some embodiments, the device 200 may include one or more actuation devices 230 operatively coupled to the polarizer 206 and configured to manipulate, move, or rotate the polarizer 206 to a desired angular configuration. The actuation device 230 may be any device configured to move or rotate the polarizer 206 and may include, but is not limited to, a mechanical, electromechanical, hydromechanical, hydraulic, or pneumatic device configured to produce mechanical motion, or an actuator or a piston and solenoid assembly. In some embodiments, the actuation device 230 may be communicably coupled to a computer system (not shown), such as the computer system arranged to receive the resulting output signal 229 discussed above. In response to the resulting output signal 229 or other parameters, the computer system may be configured to send command signals to operate the actuation device 230.

In an exemplary operation, the polarized light 208 may exhibit x-axis polarization at a first angle of rotation for the polarizer 206 and y-axis polarization at a second angle of rotation for the polarizer 206, where the first and second angles of rotation are offset from each other by 90° in either angular direction. Since the device 200 employs the birefringent ICE 214, x-axis polarized light 208 may result in an output signal 222 from the first detector 220 corresponding to a first characteristic of interest of the substance 210, whereas y-axis. polarized light 208 may result in an output signal 222 corresponding to a second characteristic of interest of the substance 210. The actuation device 230 may be configured to facilitate the change in the polarized light 208 between x-axis and y-axis polarization by rotating the polarizer 206 between the first and second angles of rotation.

In at least one embodiment, additional characteristics or analytes may be detected by rotating the polarizer 206 to a third angle of rotation between the first and second angles of rotation. For example, the polarizer 206 may be rotated to a third angle located between x-axis polarization and y-axis polarization of the polarizer 206 (i.e., between 0° and 90°) in either angular direction. In some embodiments, the output signal 222 at the third angle may correspond to a third characteristic of interest of the substance 210, and otherwise encompass at least a linear combination of the two spectra derived at both x-axis and y-axis polarizations in proportion to the amount of polarization of the polarizer 206. Rotating the polarizer to 45°, for example, may result in unpolarized light being passed through or otherwise optically interacting with the ICE 214. As a result, the third characteristic of interest may correspond to the response of the ICE 214 upon optically interacting with generally unpolarized light. Accordingly, an operator may be able to locate a regression vector that is fairly matched such that the birefringent ICE 214 could be sensitive to this third characteristic of interest.

In yet other embodiments, the polarizer 206 may be rotated to a third angle of rotation between the first and second angles of rotation to account for temperature fluctuations experienced by the ICE 214 during operation. Temperature fluctuations can adversely affect the spectra of the ICE 214, which may require expensive compensation techniques to compensate for changes in the refractive index (dN/dT) and thickness of the ICE 214 due to expansion/contraction. In at least one embodiment, the polarizer 206 may be rotated to a third angle located between x-axis polarization and y-axis polarization of the polarizer 206 (i.e., between 0° and 90°) in either angular direction to correct for dN/dT and expansion/contraction effects due to temperature fluctuations. As a result, each ICE component may be able to be used over a broader temperature range. Similar manipulations to the polarizer 206 may be implemented to compensate for other parameters, such as the temperature of the optical computing device 200 as a whole, the temperature of the substance 210, pressure in the system, density, and other parameters, without departing from the scope of the disclosure.

In other embodiments, the ICE 214 may be designed such that x-polarization is configured to detect a particular characteristic or analyte of interest at relatively low temperatures experienced by the ICE 214, and y-polarization is configured to detect the same analyte of interest at relatively high temperatures. The low temperatures may be, for example, temperatures ranging below about 100° C. and the high temperatures may be, for example, temperatures ranging above about 100° C. Such temperature ranges may range above and below 100° C., without departing from the scope of the disclosures, and are provided herein for illustrative purposes only in describing the current embodiment. According to such embodiments, the polarizer 206 may be rotated to a third angle located between x-axis polarization and y-axis polarization of the polarizer 206 (i.e., between 0° and 90°) in either angular direction to correct for dN/dT and expansion/contraction effects due to temperature fluctuations.

Accordingly, the birefringent ICE 214 in conjunction with the polarizer 206 allows the optical computing device 200 to measure the concentrations of at least two different analytes, one in response to x-polarized light and the second in response to y-polarized light. In other embodiments, the optical computing device 200 may be configured to measure the concentration of additional analytes by rotating the polarizer 206 to a rotational angle between the x-axis and y-axis polarization angles of the polarizer 206. In yet other embodiments, the polarizer 206 may be rotated to a rotational angle between the x-axis and y-axis polarization angles in order to compensate for temperature fluctuations. As a result, an optical computing device that employs a single ICE component may now be able to increase the number of analytes that are measurable, and may be able to be fine tuned for various environmental applications.

Moving various components of the device 200 within the described optical train may produce a substantially equal result in the form of the output signal 222. For example, optically interacting the electromagnetic radiation 204 either directly or indirectly with each of the polarizer 206, the substance 210, and the birefringent ICE 214 may result in optically interacted light being conveyed to the first detector 220. In the embodiment of FIG. 2, the transmitted light 216 generated by the birefringent ICE 214 may be characterized as optically interacted light, since it represents optical interaction of each of the polarizer 206, the substance 210, and the birefringent ICE 214. As long as the first detector 220 receives such optically interacted light, the resulting output signal 222 will be substantially the same in providing information about at least two characteristics of interest of the substance 210.

Accordingly, while the device 200 of FIG. 1 is described as generating various distinct beams of electromagnetic radiation or light (i.e., polarized light 208, sample-interacted light 212, and transmitted light 216, etc.) in a particular series or steps, those skilled in the art will readily recognize that each of these beams are a direct or indirect reaction to the electromagnetic radiation 204 as emitted from the electromagnetic source 202, and their combination results in optically interacted light being delivered or otherwise conveyed to the first detector 220. Some substances 210, such as a sugar solution for example, may be optically active and change the polarization state of transmitted light. For such substances 210, it may prove advantageous to pass unpolarized light through the substance 210 which will result in sample-interacted unpolarized light being emitted from the substance 210 to be transmitted through the polarizer 206, the birefringent ICE 214, and the remaining optical train components of the particular optical computing device. Consequently, variations to the structural placement of such components within the optical train of the device 200 are contemplated as being within the scope of this disclosure, as illustrated in the following figures.

Figure 3:
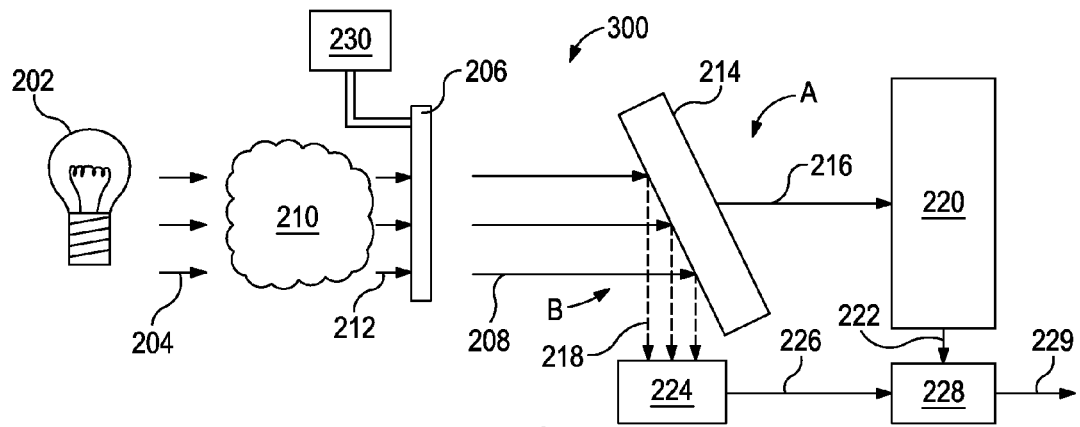
FIG. 3 illustrates another exemplary optical computing device, according to one or more embodiments.

Referring now to FIG. 3, illustrated is another exemplary optical computing device 300, according to one or more embodiments of the disclosure. The optical computing device 300 may be similar in some respects to the optical computing device 200 of FIG. 2 and therefore may be best understood with reference thereto, where like numerals represent like elements not described again in detail. In FIG. 3, the position of the polarizer 206 is moved in the optical train of the device 300 such that it receives the sample interacted light 212 from the substance 210 and conveys the resulting polarized light 208 to the birefringent ICE 214.

The resulting effect is the same as the first detector 220 receives optically interacted light with either x-axis polarization or y-axis polarization. In particular, the polarized light 208 may exhibit x-axis polarization at the first angle of rotation or y-axis polarization at the second angle of rotation corresponding to the polarizer 206. As a result, x-axis or y-axis polarized light 208 may impinge upon the birefringent ICE 214 and the optically interacted light, in the form of the transmitted light 216, is received by the first detector 220 and the output signal 222 may correspond to at least two different analytes of interest of the substance 210. Moreover, rotating the polarizer 206 to a third angle of rotation between the x-axis and y-axis polarizations may result in the detection of at least a third analyte of interest of the substance 210.

Figure 4:
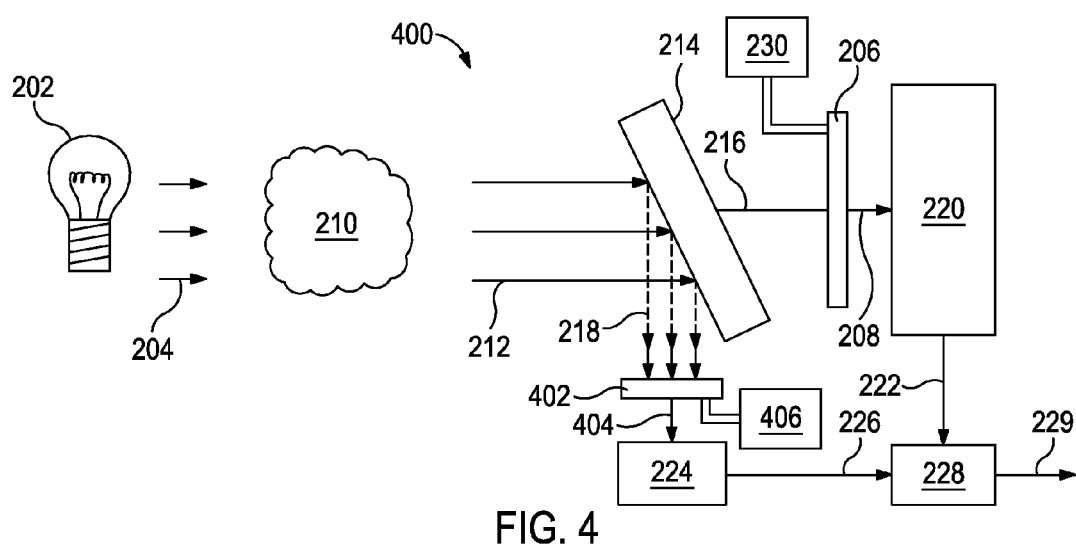
FIG. 4 illustrates another exemplary optical computing device, according to one or more embodiments.

Referring to FIG. 4, illustrated is another exemplary optical computing device 400, according to one or more embodiments of the disclosure. The optical computing device 400 may be similar in some respects to the optical computing devices 200 and 300 of FIGS. 2 and 3, respectively, and therefore may be best understood with reference thereto, where like numerals represent like elements. In FIG. 4, the position of the polarizer 206 is moved in the optical train of the device 400 to after the birefringent ICE 214 such that the transmitted light 216 is received by the polarizer 206 and the polarized light 208 is provided directly to the first detector 220.

As long as there is optical interaction with the substance 210 and each of the birefringent ICE 214 and the polarizer 206, optically interacted light may be provided to the first detector 220 and the output 222 therefrom will be substantially the same. For example, the transmitted light 216 optically interacts with the polarizer 206 such that the polarized light 208 becomes the optically interacted light conveyed to the first detector 220. As a result, the polarized light 208 resulting from the transmitted light 216 in FIG. 4 may exhibit x-axis polarization at the first angle of rotation or y-axis polarization at the second angle of rotation corresponding to the polarizer 206, and the output signal 222 may correspond to at least two different analytes of interest of the substance 210. Additionally, rotating the polarizer 206 to a third angle of rotation between the x-axis and y-axis polarizations may result in the detection of and output 222 corresponding to at least a third analyte of interest of the substance 210.

In at least one embodiment, the device 400 may further include a second polarizer 402 configured to receive the reflected light 218 and emit or otherwise provide a second beam of polarized light 404 to the second detector 224. Similar to the first polarizer 206, the second polarizer 402 may be configured to rotate such that different degrees of polarized light 404 may be provided to the second detector 224. In some embodiments, a second actuation device 406 may be included in the device 400 and operatively coupled to the second polarizer 402 such that the angular configuration of the second polarizer 402 may be manipulated. The second actuation device 406 may be similar to the first actuation device 230, and therefore will not be described again in detail. In some embodiments, however, the first and second actuation devices 230, 406 may be one and the same and configured to rotate each of the first and second polarizers 206, 402 jointly or independently.

In some embodiments, the rotation of the two polarizers 206, 402 may be coordinated so that they are both transmitting light with the same polarization state to the respective detectors 220, 224. Coordinating the two polarizers 206, 402 is useful, since the output signal 222 and the compensating signal 226 will be generated using the same polarization, which will result in accurate normalization of the output signal 222.

Figure 5:
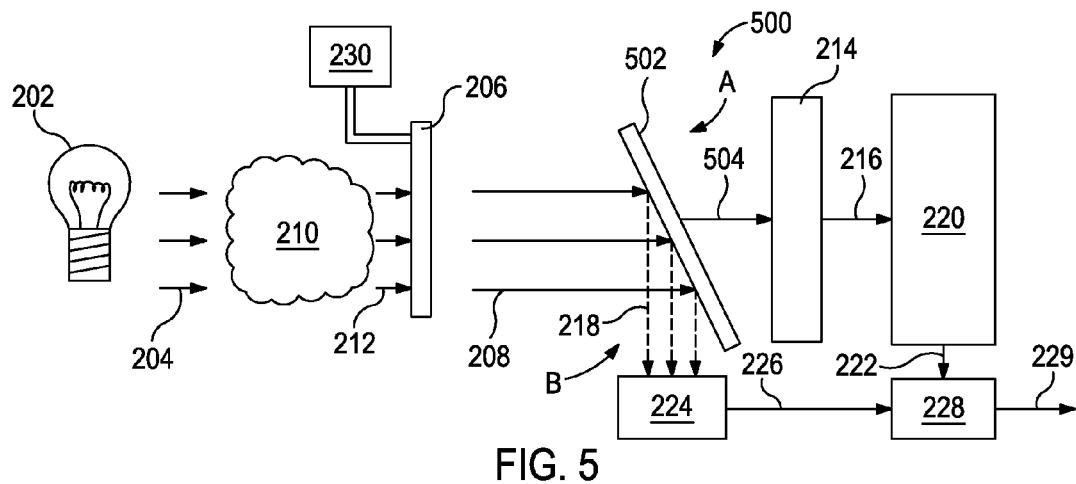
FIG. 5 illustrates another exemplary optical computing device, according to one or more embodiments.

Referring now to FIG. 5, illustrated is another exemplary optical computing device 500, according to one or more embodiments of the disclosure. The optical computing device 500 may be similar in some respects to the optical computing device 300 of FIG. 3, and therefore may be best understood with reference thereto, where like numerals again represent like elements. The optical computing device 500 includes a beam splitter 502 configured to receive the polarized light 208 and produce the reflected light 218 in the B channel and convey a transmitted beam 504 in the A channel toward the birefringent ICE 214.

The beam splitter 502 may be arranged within the device 500 at other locations along the optical train without departing from the scope of the disclosure. For example, it is also contemplated herein to arrange the beam splitter 502 prior to the substance 210, prior to the polarizer 206, or after the birefringent ICE 214. In each of these alternative configurations, the electromagnetic radiation 204 is able to optically interact directly or indirectly with each of the polarizer 206, the substance 210, and the birefringent ICE 214, and therefore the output signal 222 generated by the first detector 220 will be substantially the same in providing data about at least two characteristics of interest.

Figure 6:
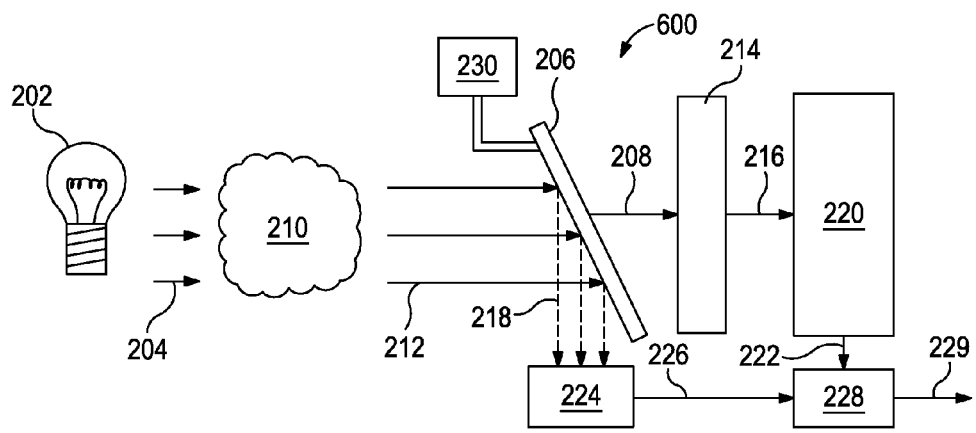
FIG. 6 illustrates another exemplary optical computing device, according to one or more embodiments.

Referring now to FIG. 6, illustrated is another exemplary optical computing device 600, according to one or more embodiments of the disclosure. The optical computing device 600 may be similar in some respects to the optical computing device 500 of FIG. 5, and therefore may be best understood with reference thereto, where like numerals again represent like elements. Unlike the device 500 of FIG. 5, the beam splitter 502 is omitted from the optical computing device 600 and otherwise replaced with the polarizer 206 that acts as a beam splitter. Accordingly, the polarizer 206 may be characterized as a "polarizing beam splitter." As illustrated, the polarizer 206 may be arranged at an angle of incidence (e.g., 45°) with respect to the sample interacted light 212 such that it is able to receive the sample interacted light 212 and generate transmitted polarized light 208 and reflected polarized light 218.

The angle of incidence is advantageous in eliminating the need for the actuation device 230 to be used to manipulate the angle of rotation of the polarizer 206 in order to obtain both x and y polarized light. Instead, the polarizer 206 may automatically divide the sample interacted light 212 into x and y polarizations. In particular, the transmitted polarized light 208 may exhibit x polarization and the reflected polarized light 218 may exhibit y polarization, or vice versa, without departing from the scope of the disclosure. In such embodiments, the resulting signals in each channel may be deconvolved in order to obtain a reference signal used to normalize each signal for radiating deviations.

In some embodiments, the actuation device 230 may nonetheless be configured to manipulate the angle of rotation for the polarizer 206, thereby allowing the output signal 222 to be indicative of additional characteristics of interest corresponding to a linear combination between the x and y polarizations, as generally described above. The angle of incidence or tilt of the polarizer 206 may vary depending on the application and other structural considerations of the device 600. In some embodiments, for instance, the actuation device 230 may further be configured to manipulate the tilt of the polarizer 206. Accordingly, it is also contemplated herein to have an angle of incidence that varies from 45°, either greater or lesser, without departing from the scope of the disclosure.

Figure 7:
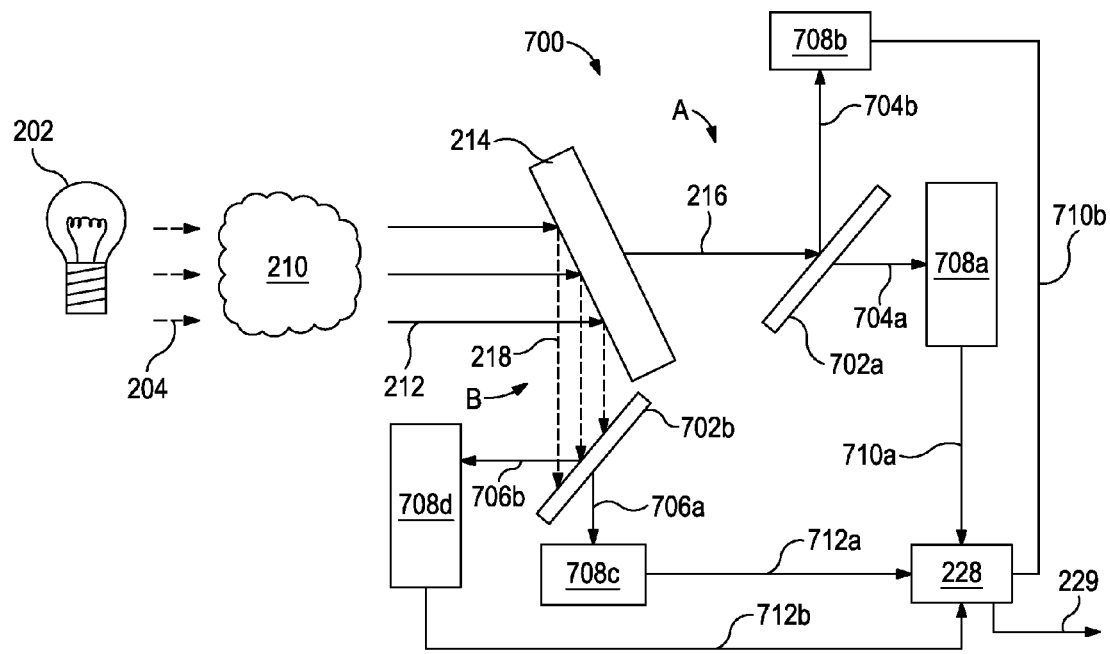
FIG. 7 illustrates another exemplary optical computing device, according to one or more embodiments.

Referring now to FIG. 7, illustrated is another exemplary optical computing device 700, according to one or more embodiments of the disclosure. The optical computing device 700 may be similar in some respects to the optical computing devices 300 and 400 of FIGS. 3 and 4, and therefore may be best understood with reference thereto where like numerals represent like elements. As illustrated, the device 700 may include the birefringent ICE 214 employed in at least one aspect as a beam splitter that simultaneously produces both the transmitted light 216 and the reflected light 218. The transmitted light 216 may be conveyed to and otherwise received by a first polarizer 702a, and the reflected light 218 may be conveyed to and otherwise received by a second polarizer 702b. The first and second polarizers 702a,b may be substantially similar to the polarizer 206 described above and therefore will not be described again.

Similar to the polarizer 206 depicted in the device 600 of FIG. 6, the first and second polarizers 702a,b may be characterized as corresponding polarizing beam splitters configured to both transmit and reflect polarized light. In particular, the first polarizer 702a may be configured to receive the transmitted light 216 and generate a first beam of transmitted polarized light 704a and a first beam of reflected polarized light 704b. Similarly, the second polarizer 702b may be configured to receive the reflected light 218 and generate a second beam of transmitted polarized light 706a and a second beam of reflected polarized light 706b.

As illustrated, each of the polarizers 702a,b may be arranged within the device 700 at corresponding angles of incidence (e.g., 45°) with respect to the transmitted light 216 and the reflected light 218, respectively. Again, the angle of incidence of each polarizer 702a,b may vary from 45° depending on the application and other structural considerations of the device 700. Such an angle of incidence, however, may prove advantageous in eliminating the need for an actuation device used to manipulate the angle of rotation of the polarizers 702a,b in order to obtain both x and y polarized light. Instead, the polarizers 702a,b, acting as polarizing beam splitters, may be configured to automatically divide the incoming light beam into x and y polarizations. In particular, the transmitted polarized light 704a may exhibit x polarization and the reflected polarized light 704b may exhibit y polarization. Similarly, the transmitted polarized light 706a may exhibit x polarization and the reflected polarized light 706b may exhibit y polarization.

As illustrated with respect to the A channel, the transmitted polarized light 704a may be directed to a first detector 708a and the reflected polarized light 704b may be directed to a second detector 708b, thereby providing x polarized light to the first detector 708a and y polarized light to the second detector 708b. In other words, the transmitted polarized light 704a may be characterized as transmitted optically interacted light and the reflected polarized light 704b may be characterized as reflected optically interacted light. The first and second detectors 708a, 708b may be similar to the first and/or second detectors 220, 224 described above and therefore will not be described again. The resulting polarization of the transmitted light 216 as optically interacting with the first polarizer 702a allows the first and second detectors 708a,b to detect both characteristics of interest of the substance 210 simultaneously without having to rotate or otherwise manipulate the position of the polarizer 702a. As illustrated, the first detector 708a may generate a first output signal 710a and the second detector 708b may generate a second output signal 710b, where each output signal 710a,b is communicated to the signal processor 228 and corresponds to the first and second characteristics of interest of the substance 210, respectively.

Similarly, in the B channel the reflected polarized light 218 may be divided into x and polarized light in the form of the transmitted polarized light 706a and y polarized light in the form of the reflected polarized light 706b. The transmitted polarized light 706a may be directed to a third detector 708c and the reflected polarized light 706b may be directed to a fourth detector 708d. The third and fourth detectors 708c, d may also be similar to the first and/or second detectors 220, 224 described above and therefore will not be described again. In some embodiments, the B channel may be used as a reference channel, as generally described above. In such embodiments, one or both of the third and fourth detectors 708c, d may provide compensating signals 712a and 712b to the signal processor 228 for normalizing the output signals 710a,b, for example. Moreover, in such embodiments, the second polarizer 702b may be replaced with a beam splitter or omitted entirely from the device 700 without departing from the scope of the disclosure.

In other embodiments, however, the function of the A and B channels may be reversed, and the B channel may instead be used to monitor and detect the at least two characteristics of interest corresponding to the x and y polarizations, as derived through the second polarizer 702b. In such embodiments, the resulting polarization of the reflected light 218 as optically interacting with the second polarizer 702b allows the third and fourth detectors 708c, d to detect both characteristics of interest of the substance 210 simultaneously without having to rotate the polarizer 702b. Moreover, in such embodiments, the compensating signals 712a,b may instead encompass output signals, similar to the first and second output signals 710a,b and communicated to the signal processor 228 to determine specific concentrations of the first and second characteristics of interest, respectively.

Referring now to FIGS. 8A and 8B, with continued reference to the above-described figures and embodiments, illustrated is a portion of an exemplary optical train 800, according to one or more embodiments. The optical train 800 may include components similar in some respects to the various components described above in FIGS. 2-7. As illustrated, for example, the optical train 800 may include a polarizer module 802, an ICE module 804, and a detector module 806. The optical train 800 may be incorporated into any of the optical computing devices 200-700 described herein, for the purpose of detecting at least two characteristics of interest of a substance 210. For example, the polarizer module 802 may replace the above-described polarizer 206, the ICE module 804 may replace the above-described birefringent ICE 214, and the detector module 806 may replace the above-described first and second detectors 220, 224, without departing from the scope of the disclosure.

The polarizer module 802 may be a rotatable polarizer configured to rotate in the direction indicated by the arrow A in order to change its phase position. Similar to the polarizer 206 described above, the polarizer module 802 may be moved or otherwise manipulated using one or more actuation devices (not shown) or the like. As illustrated, the polarizer module 802 may define a central aperture 808 that is divided into at least four sectors including a blank sector 810a, an opaque sector 810b, an x polarizing sector 810c, and a y polarizing sector 810d. The blank sector 810a may be a blank piece of glass, plastic, or other transparent material configured to allow the electromagnetic radiation 204 (either directly or indirectly) to pass therethrough unobstructed, unadulterated, or otherwise un-polarized. In other embodiments, the blank sector 810a may simply be a hole defined in the polarizer module 802 that serves a substantially similar purpose. Similar to the B channel described above, the blank sector 810a may prove useful in providing electromagnetic radiation 204 or light for the purpose of normalizing output signals from the detector module 806. In other embodiments, the blank sector 810a may pass unpolarized light that can be used for measuring a third characteristic or analyte of interest.

The opaque sector 810b may be a portion of the polarizer module 802 configured to substantially prevent the electromagnetic radiation 204 from passing therethrough. In some embodiments, for example, the opaque sector 810b may encompass a non-transmissive substrate, such as a painted piece of glass or plastic, or the like. In other embodiments, the opaque sector 810b may be a solid structural portion of the polarizer module 802 that prevents the electromagnetic radiation 204 from directly or indirectly passing therethrough over the arcuate section of the polarizer module 802. In operation, the opaque sector 810b serves to move the resulting signals from DC mode to AC mode, since DC signals tend to drift over time. Moreover, the opaque sector 810b serves to provide a measurement of "dark current." When no light is impinging on a detector, a small signal may nonetheless be generated. Since the output of photodiode detectors is usually a current, this unwanted, spurious signal is typically referred to as dark current. Such dark current should be subtracted from signals corresponding to the analytes of interest, and the opaque sector 810b helps facilitate this process.

The x polarizing sector 810c may be an optical filter that passes electromagnetic radiation 204 transmitted in the x-direction, but blocks waves of other polarizations. The optical filter may be disposed on a substrate, such as glass, plastic, or a film, that is configured for x polarization of light. Similarly, the y polarizing sector 810d may be an optical filter that passes electromagnetic radiation 204 transmitted in the y-direction, but blocks waves of other polarizations.

The ICE module 804 may include a plurality of apertures (four shown) corresponding to the plurality of sectors 810a-d of the polarizer module 802. In the illustrated embodiment, the ICE module 804 defines a first aperture having a first ICE 812a arranged therein, a second aperture having a second ICE 812b arranged therein, a third aperture having a third ICE 812c arranged therein, and a fourth aperture 812d either being empty or having a clear or transparent substrate arranged therein. Each of the first, second, and third ICE 812a-c may be substantially similar to the ICE 214 described above, and therefore each may be characterized as a birefringent ICE component. In other embodiments, however, at least one of the first, second, and third ICE 812a-c may be a traditional ICE component, without departing from the scope of the disclosure.

Similar to the ICE module 804, the detector module 806 may also define a plurality of apertures corresponding to the plurality of sectors 810a-d of the polarizer module 802. More particularly, however, the plurality of apertures of the detector module 806 may be configured to generally align optically with the apertures of the ICE module 804. In the illustrated embodiment, the detector module 806 defines a first aperture having a first detector 814a arranged therein, a second aperture having a second detector 814b arranged therein, a third aperture having a third detector 814c arranged therein, and a fourth aperture having a fourth detector 814d arranged therein. Each of the first, second, third, and fourth detectors 814a-d may be substantially similar to the detectors 220, 224 described above, and therefore will not be described again.

In an exemplary operation of the optical train 800, electromagnetic radiation 204 impinges first on the polarizer module 802. The position of the polarizer module 802, however, may be switched with the ICE module 804 such that the electromagnetic radiation 204 impinges first on the ICE module 804, without departing from the scope of the disclosure. In the illustrated embodiment, the electromagnetic radiation 204 impinges on the polarizer module 802 and three beams of light corresponding to the blank sector 810a, the x polarizing sector 810c, and the y polarizing sector 810d are transmitted toward the ICE module 804. As discussed above, the opaque sector 810b prevents light from passing through the polarizer module 802 over that section.

The unadulterated or un-polarized beam of light transmitted through the blank sector 810a is conveyed to the fourth aperture 812d of the ICE module 804 and from there conveyed to and received by the fourth detector 814d. Since this un-polarized beam of light passes through the fourth aperture 812d, which is either empty or has a clear or transparent substrate arranged therein, the light may be used as a reference light to detect any radiating deviations stemming from the electromagnetic radiation source 202 (not shown). Consequently, similar to the second detector 224 of FIGS. 2-6, the fourth detector 814*d* may be used as a reference detector for this phase position of the polarizer module 802.

The x polarized light that is transmitted through the x polarization sector 810*c* is conveyed to the first ICE 812*a* of the ICE module 804 and from there conveyed to and received by the first detector 814*a*. Accordingly, in the phase position of the polarizer module 802 illustrated in FIG. 8A, the first detector 814*a* may be configured to receive x polarized light after having optically interacted with the first ICE 812*a*. As a result, the first detector 814*a* may be able to determine a first analyte or characteristic corresponding to the first ICE 812*a* as having transmitted x polarized light.

Similarly, the y polarized light that is transmitted through the y polarization sector 810*d* is conveyed to the third ICE 812*c* of the ICE module 804 and from there conveyed to and received by the third detector 814*c*. Accordingly, in the phase position depicted in FIG. 8A, the third detector 814*c* may be configured to receive y polarized light after having optically interacted with the third ICE 812*c*. As a result, the third detector 814*c* may be able to determine a first analyte or characteristic corresponding to the third ICE 812*c* as having transmitted y polarized light.

In this same phase position, the second ICE 812*b* does not receive any light since the electromagnetic radiation 204 is blocked at the opaque sector 810*b*.

Referring now to FIG. 8B, illustrated is a new phase position of the polarizer module 802. Specifically, the polarizer module 802 is depicted as having been rotated by about 90° in the direction of the arrow A such that each of the sectors 801*a-d* now align with different portions of both of the ICE module 804 and detector module 806. In particular, the blank sector 810*a* now aligns with and transmits electromagnetic radiation 204 to the first ICE 812*a* and the first detector 814*a*, the x polarizing sector 810*c* now aligns with the second ICE 812*b* and the second detector 814*b*, and the y polarizing sector 810*d* now aligns with the fourth aperture 812*d* and the fourth detector 814*d*. Although aligned with the third ICE 812*c* and the third detector 814*c*, the opaque sector 810*b* again substantially blocks any electromagnetic radiation 204 from transmitting through the polarizer module 802.

In the phase position of FIG. 8B, the first ICE 812*a* receives un-polarized light and transmits optically interacted light to the first detector 814*a* which provides an output signal indicative of a characteristic or analyte corresponding to the first ICE 812*a* having optically interacted with unpolarized light. The y polarized light that is transmitted through the y polarization sector 810*d* is conveyed through the fourth aperture 812*d* of the ICE module 804 and from there conveyed to and received by the fourth detector 814*d*. Since the y polarized light does not optically interact with an ICE component, but instead passes through the fourth aperture 812*d*, the fourth detector 814*d* may be used as a reference source to detect radiating deviations and be used to normalize the device response.

In this same phase position, x polarized light transmitted through the x polarization sector 810*c* is conveyed to the second ICE 812*b* of the ICE module 804 and from there conveyed to and received by the second detector 814*b*. Accordingly, in the depicted phase position of the polarizer module 802, the second detector 814*b* may be configured to receive x polarized light after having optically interacted with the second ICE 812*b*. As a result, the second detector 814*b* may be able to determine a first analyte or characteristic corresponding to the second ICE 812*b* as having transmitted x polarized light.

In a continued exemplary operation, the phase position of the polarizer module 802 may be shifted an additional 90° such that each of the sectors 810*a-d* align with different portions of both of the ICE module 804 and detector module 806. It will be appreciated that continual shifting of the phase position of the polarizer module 802 about a complete 360° rotation will result in x and y polarized light being transmitted through each of the first, second, and third ICE 812*a-c* and thereafter received by the corresponding first, second, and third detectors 814*a-c* after having optically interacted with each ICE 812*a-c*. As a result, over the course of a full 360° phase position rotation of the polarizer module 802, the first, second, and third detectors 814*a-c* may be able to detect at least two analytes or characteristics of interest of the substance 210 (not shown) as corresponding to each of the first, second, and third ICE 812*a-c*.

Such results are depicted graphically in FIG. 9. In FIG. 9, a line chart 900 is depicted showing detector signal results over a full 360° revolution of the polarizer module 802. As one example, and with continued reference to the phase positions of FIGS. 8A and 8B, the signal for the fourth detector 814*d* is shown at 2 over the phase covering time $t_0$ to time $t_1$ and gradually dropping to about 1 over the phase covering time $t_1$ to time $t_2$. This phase corresponds to the phase depicted in FIG. 8A, where the electromagnetic radiation 204 passes through the polarizer module 802 and the ICE module 804 unobstructed, but as the polarizer module 802 continues to rotate, the y polarization sector 810*d* begins to transmit light, and the resulting signal drops to around 1. This phase position is depicted in FIG. 8B.

Over the phase covering time $t_3$ to time $t_4$, the polarizer module 802 continues to rotate in the direction of arrow A (FIGS. 8A and 8B) and the signal for the fourth detector 814*d* gradually drops from about 1 to about zero as the opaque sector 810*b* eventually occludes the electromagnetic radiation 204 directed to the fourth detector 814*d*. Over the phase covering time $t_5$ to time $t_6$, the polarizer module 802 continues to rotate and the signal for the fourth detector 814*d* gradually increases back to around 1 as the x polarization sector 810*c* aligns with both the fourth ICE 812*d* and the fourth detector 814*d*. Over the phase covering time $t_7$ to time $t_8$, the polarizer module 802 continues to rotate and the signal for the fourth detector 814*d* gradually increases back to around 2 as the blank sector 810*a* is again moved into position to align with both the fourth ICE 812*d* and the fourth detector 814*d*.

Those skilled in the art will be able to read the signal results provided in the line chart 900 for each of the other detectors 814*a-c* and determine at which phase or to what degree of rotation the polarizer module 802 has been moved. Accordingly, the exemplary optical train 800 of FIGS. 8A and 8B may be configured to provide concentrations of at least six characteristics of interest, corresponding to the three ICE components 812*a-c* arranged therein. Additional ICE components may be employed in the ICE module 804, and additional corresponding detectors in the detector module 806, in order to monitor or otherwise determine additional characteristics of interest.

The computers and signal processors described herein may include computer hardware used to implement the various computations and operations required to accurately detect a desired analyte of interest. The computer hardware may include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein, including the general movement of the polarizers between x and y polarization angles, data collection from the various detectors, and normalizing the detected signals. Thus, the present embodiments are not limited to any specific combination of hardware and/or software.

As used herein, a machine-readable medium refers to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. An optical element used in an optical computing device to determine a characteristic of a substance. The optical element may include an optical substrate and at least one anisotropic layer disposed on the optical substrate.

B. An optical computing device that may include a polarizer configured to generate at least x polarized light and y polarized light, and at least one birefringent integrated computational element configured to optically interact with a substance and the polarizer, thereby generating optically interacted light. The optical computing device may also include at least one detector arranged to receive the optically interacted light and generate output signals corresponding to at least two characteristics of the substance.

C. A method of monitoring a substance. The method may include optically interacting at least one birefringent integrated computational element with at least a substance and a polarizer, thereby generating optically interacted light, the polarizer being configured to generate at least x polarized light and y polarized light. The method may also include receiving the optically interacted light with at least one detector, and generating with the at least one detector output signals corresponding to at least two characteristics of the substance.

Each of embodiments A, B, and C may have one or more of the following additional elements in any combination: Element 1: at least one isotropic layer deposited on the optical substrate in conjunction with the at least one anisotropic layer. Element 2: the at least one anisotropic layer comprises a plurality of anisotropic layers and the at least one isotropic layer comprises a plurality of isotropic layers, and wherein the plurality of anisotropic layers alternate with the plurality of isotropic layers. Element 3: the at least one anisotropic layer contains a birefringent material selected from the group consisting of beryl, calcite, calomel, ice, lithium niobate, magnesium fluoride, ruby, rutile, sapphire, sodium nitrate, tourmaline, zircon, silicon carbide, plastics, borax, epsom salt, biotite, muscovite, olivine, perovskite, topaz, ulexite, and any combination thereof. Element 4: the plastics include cellophane, polystyrene, and polycarbonate. Element 5: each layer of the plurality of isotropic layers contains a material selected from the group consisting of silicon, niobia, niobium, germanium, germania, MgF, SiO, and any combination thereof. Element 6: the at least one anisotropic layer comprises a stress induced birefringent material containing an isotropic material that has been mechanically stressed in order to generate the stress induced birefringent material.

Element 6: at least one isotropic layer is disposed on the optical substrate in conjunction with the at least one anisotropic layer. Element 7: the at least one anisotropic layer comprises a plurality of anisotropic layers and the at least one isotropic layer comprises a plurality of isotropic layers, and wherein the plurality of anisotropic layers alternate with the plurality of isotropic layers. Element 8: the at least one anisotropic layer comprises a stress induced birefringent material containing an isotropic material that has been mechanically stressed in order to generate the stress induced birefringent material. Element 9: the at least two characteristics of the substance comprise a first characteristic when the polarizer generates x polarized light and a second characteristic when the polarizer generates y polarized light. Element 10: an actuation device operatively coupled to the polarizer and configured to move the polarizer to a first angle of rotation such that the polarizer generates the x polarized light and to a second angle of rotation such that the polarizer generates the y polarized light. Element 11: the at least two characteristics comprise a characteristic detected when the actuation device moves the polarizer to a third angle of rotation between the first and second angles of rotation. Element 12: the actuation device is configured to move the polarizer to a third angle of rotation between the first and second angles of rotation in order to compensate for temperature fluctuations. Element 13: an electromagnetic radiation source configured to emit electromagnetic radiation that optically interacts with the substance. Element 14: the at least one detector comprises a first detector and a second detector arranged to detect the electromagnetic radiation and thereby generate a compensating signal indicative of electromagnetic radiating deviations. Element 15: a signal processor communicably coupled to the first and second detectors, the signal processor being configured to receive and computationally combine the output signals and the compensating signals in order to normalize the output signals. Element 16: the polarizer is arranged at an angle of incidence such that it transmits one of the x polarized light and y polarized light and reflects the other of the x polarized light and y polarized light. Element 17: the optically interacted light comprises transmitted optically interacted light derived from the x polarized light transmitted through the polarizer and reflected optically interacted light derived from the y polarized light reflected from the polarizer. Element 18: the at least one detector comprises a first detector configured to receive the transmitted optically interacted light, and a second detector configured to receive the reflected optically interacted light.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners by those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. An integrated computing element for an optical computing device, the integrated computing element comprising:
    an optical substrate; and
    at least one anisotropic layer disposed on the optical substrate, the at least one anisotropic layer arranged on the optical substrate based on a spectrum related to a characteristic of a substance.

2. The integrated computing element of claim 1, further comprising at least one isotropic layer deposited on the optical substrate in conjunction with the at least one anisotropic layer.

3. The integrated computing element of claim 2, wherein the at least one anisotropic layer comprises a plurality of anisotropic layers and the at least one isotropic layer comprises a plurality of isotropic layers, and wherein the plurality of anisotropic layers alternate with the plurality of isotropic layers.

4. The integrated computing element of claim 3, wherein each layer of the plurality of isotropic layers contains a material selected from the group consisting of silicon, niobia, niobium, germanium, germania, MgF, SiO, and any combination thereof.

5. The integrated computing element of claim 1, wherein the at least one anisotropic layer contains a birefringent material selected from the group consisting of beryl, calcite, calomel, ice, lithium niobate, magnesium fluoride, ruby, rutile, sapphire, sodium nitrate, tourmaline, zircon, silicon carbide, plastics, borax, epsom salt, biotite, muscovite, olivine, perovskite, topaz, ulexite, and any combination thereof.

6. The integrated computing element of claim 1, wherein the at least one anisotropic layer comprises a stress induced birefringent material containing an isotropic material that has been mechanically stressed in order to generate the stress induced birefringent material.

7. An optical computing device, comprising:
    a polarizer configured to generate at least x polarized light and y polarized light;
    at least one birefringent integrated computational element configured to optically interact with a substance and the polarizer, thereby generating optically interacted light; and
    at least one detector arranged to receive the optically interacted light and generate output signals corresponding to at least two characteristics of the substance.

8. The optical computing device of claim 7, wherein the at least one birefringent integrated computational element comprises:
    an optical substrate; and
    at least one anisotropic layer disposed on the optical substrate.

9. The optical computing device of claim 8, further comprising at least one isotropic layer disposed on the optical substrate in conjunction with the at least one anisotropic layer.

10. The optical computing device of claim 9, wherein the at least one anisotropic layer comprises a plurality of anisotropic layers and the at least one isotropic layer comprises a plurality of isotropic layers, and wherein the plurality of anisotropic layers alternate with the plurality of isotropic layers.

11. The optical computing device of claim 8, wherein the at least one anisotropic layer contains a birefringent material selected from the group consisting of beryl, calcite, calomel, ice, lithium niobate, magnesium fluoride, ruby, rutile, sapphire, sodium nitrate, tourmaline, zircon, silicon carbide, plastics, borax, epsom salt, biotite, muscovite, olivine, perovskite, topaz, ulexite, and any combination thereof.

12. The optical computing device of claim 8, wherein the at least one anisotropic layer comprises a stress induced birefringent material containing an isotropic material that has been mechanically stressed in order to generate the stress induced birefringent material.

13. The optical computing device of claim 7, wherein the at least two characteristics of the substance comprise a first characteristic when the polarizer generates x polarized light and a second characteristic when the polarizer generates y polarized light.

14. The optical computing device of claim 7, further comprising an actuation device operatively coupled to the polarizer and configured to move the polarizer to a first angle of rotation such that the polarizer generates the x polarized light and to a second angle of rotation such that the polarizer generates the y polarized light.

15. The optical computing device of claim 14, wherein the at least two characteristics comprise a characteristic detected when the actuation device moves the polarizer to a third angle of rotation between the first and second angles of rotation.

16. The optical computing device of claim 14, wherein the actuation device is configured to move the polarizer to a third angle of rotation between the first and second angles of rotation in order to compensate for temperature fluctuations.

17. The optical computing device of claim 7, further comprising:
an electromagnetic radiation source configured to emit electromagnetic radiation that optically interacts with the substance, wherein the at least one detector comprises a first detector and a second detector arranged to detect the electromagnetic radiation and thereby generate a compensating signal indicative of electromagnetic radiating deviations; and
a signal processor communicably coupled to the first and second detectors, the signal processor being configured to receive and computationally combine the output signals and the compensating signals in order to normalize the output signals.

18. The optical computing device of claim 7, wherein the polarizer is arranged at an angle of incidence such that it transmits one of the x polarized light and y polarized light and reflects the other of the x polarized light and y polarized light.

19. The optical computing device of claim 18, wherein the optically interacted light comprises transmitted optically interacted light derived from the x polarized light transmitted through the polarizer and reflected optically interacted light derived from the y polarized light reflected from the polarizer.

20. The optical computing device of claim 19, wherein the at least one detector comprises a first detector configured to receive the transmitted optically interacted light, and a second detector configured to receive the reflected optically interacted light.

21. A method of monitoring a substance, comprising:
optically interacting at least one birefringent integrated computational element with at least a substance and a polarizer, thereby generating optically interacted light, the polarizer being configured to generate at least x polarized light and y polarized light;
receiving the optically interacted light with at least one detector; and
generating with the at least one detector output signals corresponding to at least two characteristics of the substance.

22. The method of claim 21, wherein the at least two characteristics of the substance comprise at least a first characteristic and a second characteristic, the method further comprising:
detecting the first characteristic with the at least one detector when the polarizer generates x polarized light; and
detecting the second characteristic with the at least one detector when the polarizer generates y polarized light.

23. The method of claim 21, further comprising:
moving the polarizer to a first angle of rotation such that the polarizer produces the x polarized light; and
moving the polarizer to a second angle of rotation such that the polarizer produces the y polarized light.

24. The method of claim 23, wherein the at least two characteristics comprises a third characteristic, the method further comprising:

moving the polarizer to a third angle of rotation between the first and second angles of rotation; and
detecting the third characteristic with the at least one detector.

25. The method of claim 23, further comprising moving the polarizer to a third angle of rotation between the first and second angles of rotation in order to compensate for temperature fluctuations.

26. An optical computing device, comprising:
a polarizer module having at least a blank sector, an opaque sector, an x polarizing sector configured to generate x polarized light, and a y polarizing sector configured to generate y polarized light;
an integrated computational element (ICE) module having a plurality of birefringent ICE components configured to optically interact with a substance and the polarizer module; and
a detector module having a plurality of detectors optically aligned with the plurality of birefringent ICE components and configured to receive optically interacted light and generate output signals corresponding to a plurality of characteristics of the sub stance.

27. The optical computing device of claim 26, wherein the blank sector comprises at least one of a hole in the polarizer module and a transparent material arranged in the polarizer module.

28. The optical computing device of claim 26, wherein one or more of the plurality of birefringent ICE components comprises:
an optical substrate; and
at least one anisotropic layer disposed on the optical substrate.

29. The optical computing device of claim 28, further comprising at least one isotropic layer disposed on the optical substrate in conjunction with the at least one anisotropic layer.

30. The optical computing device of claim 29, wherein the at least one anisotropic layer comprises a plurality of anisotropic layers and the at least one isotropic layer comprises a plurality of isotropic layers, and wherein the plurality of anisotropic layers alternate with the plurality of isotropic layers.

31. The optical computing device of claim 28, wherein the at least one anisotropic layer contains a birefringent material selected from the group consisting of beryl, calcite, calomel, ice, lithium niobate, magnesium fluoride, ruby, rutile, sapphire, sodium nitrate, tourmaline, zircon, silicon carbide, plastics, borax, epsom salt, biotite, muscovite, olivine, perovskite, topaz, ulexite, and any combination thereof.

32. The optical computing device of claim 26, wherein each birefringent ICE component detects at least a first characteristic and a second characteristic of the plurality of characteristics of the substance, the first characteristic being detected when the corresponding birefringent ICE component optically interacts with x polarized light from the x polarizing sector, and the second characteristic being detected when the corresponding birefringent ICE component optically interacts with y polarized light from the y polarizing sector.

33. The optical computing device of claim 26, wherein the polarizer is rotatable such that the blank sector, the x polarizing sector, and the y polarizing sector optically interact with each of the plurality of birefringent ICE components.

* * * * *